(12) United States Patent
Syed

(10) Patent No.: US 10,639,179 B2
(45) Date of Patent: May 5, 2020

(54) SYSTEM FOR THE INTRAVASCULAR PLACEMENT OF A MEDICAL DEVICE

(71) Applicant: RAM MEDICAL INNOVATIONS, LLC, Spingfield, OH (US)

(72) Inventor: Mubin I. Syed, Springfield, OH (US)

(73) Assignee: RAM MEDICAL INNOVATIONS, LLC, Springfield, OH (US)

( * ) Notice: Subject to any disclaimer, the term of this patent is extended or adjusted under 35 U.S.C. 154(b) by 466 days.

(21) Appl. No.: 14/429,759

(22) PCT Filed: Nov. 21, 2013

(86) PCT No.: PCT/US2013/071271
§ 371 (c)(1),
(2) Date: Mar. 19, 2015

(87) PCT Pub. No.: WO2014/081947
PCT Pub. Date: May 30, 2014

(65) Prior Publication Data
US 2015/0245933 A1    Sep. 3, 2015

Related U.S. Application Data

(60) Provisional application No. 61/728,862, filed on Nov. 21, 2012.

(51) Int. Cl.
*A61F 2/95* (2013.01)
*A61M 25/04* (2006.01)
*A61M 25/09* (2006.01)

(52) U.S. Cl.
CPC .............. *A61F 2/95* (2013.01); *A61M 25/04* (2013.01); *A61M 25/09* (2013.01);
(Continued)

(58) Field of Classification Search
CPC ........... A61M 2025/0057; A61M 2025/09116; A61M 2025/09141; A61M 2025/09166;
(Continued)

(56) References Cited

U.S. PATENT DOCUMENTS 4,243,040 A    1/1981  Beecher
4,790,331 A   12/1988  Okada et al.
(Continued)

FOREIGN PATENT DOCUMENTS

CN    108472124 A    8/2018
CN    108472472 A    8/2018
(Continued)

OTHER PUBLICATIONS

International Search Report issued in International Application No. PCT/US2013/071271 dated Feb. 10, 2014, 2 pages.
(Continued)

*Primary Examiner* — Tan-Uyen T Ho
*Assistant Examiner* — Chima U Igboko
(74) *Attorney, Agent, or Firm* — Jennifer Hayes; Nixon Peabody LLP

(57) ABSTRACT

A system for the intravascular placement of a medical device including a guidewire having a first end and a second end, the first end having a microwhisk positional between a feeding state and a deployed state, a guidewire sheath surrounding the guidewire; and an anchoring device for cooperatively fixing the microwhisk relative to a patient. Also, the method of the intravascular placement of the medical device by inserting the medical device through the body with the guidewire and the microwhisk contained within the guidewire sheath, driving the microwhisk out of the guidewire sheath to position the microwhisk to its deployed state, and engaging the anchoring device from the
(Continued)

outside of the body through a body surface into the microwhisk, and further into a stabilizing body component.

22 Claims, 6 Drawing Sheets

(52) U.S. Cl.
CPC .............. *A61M 2025/09125* (2013.01); *A61M 2025/09175* (2013.01); *A61M 2025/09183* (2013.01); *A61M 2205/0266* (2013.01)

(58) Field of Classification Search
CPC ......... A61M 2025/09175; A61M 2025/09183; A61M 25/04; A61M 2025/0293; A61M 2025/0286; A61M 2025/028; A61M 25/02; A61F 2250/0067; A61F 2/95; A61B 17/3417; A61B 17/3468; A61B 17/3462; A61B 5/6846; A61B 5/6851; A61B 5/685; A61B 5/6879; A61B 90/11
USPC .......... 606/129, 198, 200; 600/585; 604/175
See application file for complete search history.

(56) References Cited

U.S. PATENT DOCUMENTS

| | | | |
|---|---|---|---|
| 5,070,589 A | 12/1991 | Howell et al. | |
| 5,098,707 A | 3/1992 | Baldwin et al. | |
| 5,293,772 A | 9/1994 | Carr, Jr. | |
| 5,344,426 A | 9/1994 | Lau et al. | |
| 5,419,777 A * | 5/1995 | Hofling .................. | A61B 18/24 128/831 |
| 5,428,567 A | 6/1995 | Horvath et al. | |
| 5,571,135 A | 11/1996 | Fraser et al. | |
| 5,651,366 A | 7/1997 | Liang et al. | |
| 5,662,703 A | 9/1997 | Yurek et al. | |
| 5,669,924 A | 9/1997 | Shaknovich | |
| 5,690,644 A | 11/1997 | Yurek et al. | |
| 5,718,702 A | 2/1998 | Edwards | |
| 5,720,735 A | 2/1998 | Dorros | |
| 5,766,192 A | 6/1998 | Zacca | |
| 5,807,330 A | 9/1998 | Teitelbaum | |
| 5,813,976 A | 9/1998 | Filipi et al. | |
| 5,957,901 A | 9/1999 | Mottola et al. | |
| 5,997,563 A | 12/1999 | Kretzers | |
| 6,027,462 A | 2/2000 | Greene et al. | |
| 6,059,813 A | 5/2000 | Vrba et al. | |
| 6,152,141 A * | 11/2000 | Stevens .................. | A61B 18/24 128/898 |
| 6,238,410 B1 | 5/2001 | Vrba et al. | |
| 6,245,017 B1 | 6/2001 | Hashimoto | |
| 6,245,573 B1 | 6/2001 | Spillert | |
| 6,450,964 B1 | 9/2002 | Webler | |
| 6,464,665 B1 * | 10/2002 | Heuser .................. | A61B 17/11 604/101.01 |
| 6,494,875 B1 | 12/2002 | Mauch | |
| 6,544,278 B1 | 4/2003 | Vrba et al. | |
| 6,663,613 B1 | 12/2003 | Lewis et al. | |
| 6,764,505 B1 | 7/2004 | Hossainy et al. | |
| 6,780,174 B2 | 8/2004 | Mauch | |
| 6,808,520 B1 | 10/2004 | Fouirkas et al. | |
| 6,837,881 B1 | 1/2005 | Barbut | |
| 6,929,633 B2 | 8/2005 | Evans et al. | |
| 6,932,829 B2 | 8/2005 | Majercak | |
| 6,942,682 B2 | 9/2005 | Vrba et al. | |
| 7,235,083 B1 | 6/2007 | Perez et al. | |
| 7,393,358 B2 | 7/2008 | Malewicz | |
| 7,651,520 B2 | 1/2010 | Fischell et al. | |
| 7,674,493 B2 | 3/2010 | Hossainy et al. | |
| 7,740,791 B2 | 6/2010 | Kleine et al. | |
| 7,758,624 B2 | 7/2010 | Dorn et al. | |
| 7,763,010 B2 | 7/2010 | Evans et al. | |
| 7,766,961 B2 | 8/2010 | Patel et al. | |
| 7,828,832 B2 | 11/2010 | Belluche et al. | |
| 7,842,026 B2 | 11/2010 | Cahill et al. | |
| 7,955,370 B2 | 6/2011 | Gunderson | |
| 8,092,509 B2 | 1/2012 | Dorn et al. | |
| 8,119,184 B2 | 2/2012 | Hossainy et al. | |
| 8,202,309 B2 | 6/2012 | Styrc | |
| 8,241,241 B2 | 8/2012 | Evans et al. | |
| 8,343,181 B2 | 1/2013 | Duffy et al. | |
| 8,419,767 B2 | 4/2013 | Al-Qbandi et al. | |
| 8,535,290 B2 | 9/2013 | Evans et al. | |
| 8,721,714 B2 | 5/2014 | Kelley | |
| 8,727,988 B2 | 5/2014 | Flaherty et al. | |
| 8,728,144 B2 | 5/2014 | Fearnot | |
| 8,740,971 B2 | 6/2014 | Iannelli | |
| 8,986,241 B2 | 3/2015 | Evans et al. | |
| 8,998,894 B2 | 4/2015 | Mauch et al. | |
| 9,301,830 B2 | 4/2016 | Heuser et al. | |
| 9,314,499 B2 | 4/2016 | Wang et al. | |
| 9,636,244 B2 | 5/2017 | Syed | |
| 9,855,705 B2 | 1/2018 | Wang et al. | |
| 9,980,838 B2 | 5/2018 | Syed | |
| 2001/0003985 A1 | 6/2001 | Lafontaine et al. | |
| 2001/0049534 A1 | 12/2001 | Lachat | |
| 2002/0077691 A1 | 6/2002 | Nachtigall | |
| 2002/0123698 A1 | 9/2002 | Garibotto et al. | |
| 2002/0156518 A1 | 10/2002 | Tehrani | |
| 2002/0165535 A1 | 11/2002 | Lesh | |
| 2003/0088187 A1 | 5/2003 | Saadat et al. | |
| 2003/0216721 A1 | 11/2003 | Diederich | |
| 2003/0229282 A1 | 12/2003 | Burdette | |
| 2004/0073190 A1 * | 4/2004 | Deem ...................... | A61F 2/07 604/500 |
| 2004/0087995 A1 * | 5/2004 | Copa ...................... | A61B 17/11 606/192 |
| 2004/0138734 A1 | 7/2004 | Chobotov et al. | |
| 2004/0147893 A1 | 7/2004 | MacAulay et al. | |
| 2004/0167463 A1 | 8/2004 | Zawacki et al. | |
| 2005/0043779 A1 | 2/2005 | Wilson | |
| 2005/0085841 A1 | 4/2005 | Eversull et al. | |
| 2005/0101968 A1 | 5/2005 | Dadourian | |
| 2005/0113862 A1 * | 5/2005 | Besselink ............... | A61F 2/013 606/200 |
| 2005/0222488 A1 | 10/2005 | Chang et al. | |
| 2005/0234499 A1 | 10/2005 | Olson et al. | |
| 2005/0251160 A1 * | 11/2005 | Saadat ............... | A61B 17/0401 606/153 |
| 2006/0025752 A1 | 2/2006 | Broaddus et al. | |
| 2006/0025844 A1 | 2/2006 | Majercak et al. | |
| 2006/0030923 A1 | 2/2006 | Gunderson | |
| 2006/0036218 A1 | 2/2006 | Goodson et al. | |
| 2006/0155363 A1 | 7/2006 | Laduca et al. | |
| 2006/0200221 A1 | 9/2006 | Malewicz | |
| 2006/0257389 A1 | 11/2006 | Binford | |
| 2006/0259063 A1 * | 11/2006 | Bates .................... | A61M 25/09 606/198 |
| 2006/0270900 A1 | 11/2006 | Chin et al. | |
| 2007/0016019 A1 | 1/2007 | Salgo | |
| 2007/0016062 A1 | 1/2007 | Park | |
| 2007/0038061 A1 | 2/2007 | Huennekens et al. | |
| 2007/0038293 A1 | 2/2007 | St. Goar et al. | |
| 2007/0049867 A1 | 3/2007 | Shindelman | |
| 2007/0083215 A1 | 4/2007 | Hamer et al. | |
| 2007/0118151 A1 | 5/2007 | Davidson et al. | |
| 2007/0129719 A1 | 6/2007 | Kendale et al. | |
| 2008/0039746 A1 | 2/2008 | Hissong et al. | |
| 2008/0114239 A1 | 2/2008 | Randall et al. | |
| 2008/0194993 A1 | 8/2008 | McLaren et al. | |
| 2008/0208309 A1 | 8/2008 | Saeed | |
| 2008/0281398 A1 | 11/2008 | Koss | |
| 2009/0005679 A1 | 1/2009 | Dala-Krishna | |
| 2009/0018526 A1 | 1/2009 | Power et al. | |
| 2009/0036780 A1 | 2/2009 | Abraham | |
| 2009/0093791 A1 | 4/2009 | Heuser | |
| 2009/0132019 A1 | 5/2009 | Duffy et al. | |
| 2009/0171293 A1 * | 7/2009 | Yang ...................... | A61M 25/04 604/164.04 |
| 2009/0177035 A1 | 7/2009 | Chin | |
| 2009/0240253 A1 | 9/2009 | Murray | |
| 2009/0254116 A1 | 10/2009 | Rosenschein et al. | |
| 2009/0270975 A1 | 10/2009 | Giofford, III et al. | |

(56) References Cited

U.S. PATENT DOCUMENTS

| | | |
|---|---|---|
| 2009/0319017 A1 | 12/2009 | Berez et al. |
| 2010/0016943 A1 | 1/2010 | Chobotov |
| 2010/0024818 A1 | 2/2010 | Stenzler et al. |
| 2010/0030165 A1 | 2/2010 | Takagi et al. |
| 2010/0030256 A1 | 2/2010 | Dubrul et al. |
| 2010/0069852 A1 | 3/2010 | Kelley |
| 2010/0168583 A1 | 7/2010 | Dausch et al. |
| 2010/0185161 A1 | 7/2010 | Pellegrino et al. |
| 2010/0185231 A1 | 7/2010 | Lashinski |
| 2010/0204708 A1 | 8/2010 | Sharma |
| 2010/0268067 A1 | 10/2010 | Razzaque et al. |
| 2010/0272740 A1 | 10/2010 | Vertegel et al. |
| 2010/0298922 A1 | 11/2010 | Thornton et al. |
| 2011/0009943 A1 | 1/2011 | Paul et al. |
| 2011/0034987 A1 | 2/2011 | Kennedy |
| 2011/0071394 A1 | 3/2011 | Fedinec |
| 2011/0082533 A1 | 4/2011 | Vardi et al. |
| 2011/0213459 A1 | 9/2011 | Garrison |
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0022636 A1 | 1/2012 | Chobotov |
| 2012/0029478 A1 | 2/2012 | Kurosawa |
| 2012/0034205 A1 | 2/2012 | Alkon |
| 2012/0035590 A1 | 2/2012 | Whiting et al. |
| 2012/0169712 A1 | 7/2012 | Hill et al. |
| 2012/0209375 A1 | 8/2012 | Madrid et al. |
| 2012/0220942 A1 | 8/2012 | Hall et al. |
| 2012/0289945 A1 | 11/2012 | Segermark |
| 2013/0053792 A1* | 2/2013 | Fischell ............ A61M 25/0084 604/275 |
| 2013/0131777 A1 | 5/2013 | Hartley et al. |
| 2013/0296773 A1 | 11/2013 | Feng et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0142427 A1 | 5/2014 | Petroff |
| 2014/0214002 A1 | 7/2014 | Lieber et al. |
| 2014/0228808 A1 | 8/2014 | Webster et al. |
| 2014/0358123 A1 | 12/2014 | Ueda et al. |
| 2015/0018942 A1 | 1/2015 | Hung et al. |
| 2015/0174377 A1 | 6/2015 | Syed |
| 2015/0190576 A1 | 7/2015 | Lee et al. |
| 2015/0201900 A1 | 7/2015 | Syed |
| 2015/0250991 A1 | 9/2015 | Silvestro |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1 | 5/2016 | Siegel et al. |
| 2016/0296355 A1 | 10/2016 | Syed |
| 2016/0338835 A1 | 11/2016 | Van Bladel et al. |
| 2017/0119562 A1 | 5/2017 | Syed |
| 2017/0119563 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |
| 2018/0042743 A1 | 2/2018 | Syed |
| 2018/0059124 A1 | 3/2018 | Syed |
| 2018/0116780 A1 | 5/2018 | Laine |
| 2018/0250147 A1 | 9/2018 | Syed |
| 2019/0091441 A1 | 3/2019 | Syed |
| 2019/0254675 A1 | 8/2019 | Syed |
| 2019/0255286 A1 | 8/2019 | Syed |
| 2019/0336114 A1 | 11/2019 | Syed |

FOREIGN PATENT DOCUMENTS

| | | |
|---|---|---|
| CN | 108882975 A | 11/2018 |
| CN | 109475722 A | 3/2019 |
| EP | 3280355 A1 | 2/2018 |
| EP | 3367969 A1 | 9/2018 |
| EP | 3368123 A1 | 9/2018 |
| EP | 3399944 A1 | 9/2018 |
| EP | 3405261 A1 | 11/2018 |
| IN | 201827018555 A | 10/2018 |
| IN | 201827018768 A | 10/2018 |
| WO | 1996036269 | 11/1996 |
| WO | 2004/089249 A1 | 10/2004 |
| WO | 2012030101 | 8/2006 |
| WO | 2011/011539 A1 | 1/2011 |
| WO | 2011/106502 | 9/2011 |
| WO | 2011/137336 A1 | 11/2011 |
| WO | 2010129193 A1 | 11/2011 |
| WO | 2014081947 | 5/2014 |
| WO | 2014197839 | 12/2014 |
| WO | 2016164215 | 10/2016 |
| WO | 2017/074492 A1 | 5/2017 |
| WO | 2017/074536 A1 | 5/2017 |
| WO | 2017127127 | 7/2017 |
| WO | 2017222571 A1 | 12/2017 |
| WO | 2017222612 A1 | 12/2017 |
| WO | 2018/164766 A1 | 9/2018 |
| WO | 2019/070349 A1 | 4/2019 |
| WO | 2019/160625 A1 | 8/2019 |
| WO | 2019/160626 A1 | 8/2019 |

OTHER PUBLICATIONS

Written Opinion issued in International Application No. PCT/US2013/071271 dated Feb. 10, 2014, 5 pages.
International Preliminary Report on Patentability issued in International Application No. PCT/US2013/071271 dated May 26, 2014, 6 pages.
International Search Report and Written Opinion issued for International Application No. PCT/US2017/021188 dated May 10, 2017, 11 pages.
Stroke Treatments, American Heart Association, Retrieved from: Http://www.strokeassociation.org/STROKEORG/AboutStroke/Treatment/Stroke-Treatments_UCM_310892_Article.jsp#V9Hrg2WfV_1.
Beckman et al., Venous Thromboembolism: A Public Health Concern, Am J Prev Med., 2010, vol. 38(4), pp. S495-S501.
Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.
Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.
International Search Report and Written Opinion for International Application No. PCT/US2016/024795 dated Aug. 30, 2016, 14 pages.
International Search Report and Written Opinion issued for International Application No. PCT/US2016/024794 dated Jul. 1, 2016, 10 pages.
International Search Report and Written Opinion issued for International Application No. PCT/US2016/047163 dated Oct. 28, 2016, 9 pages.
Office Action issued in U.S. Appl. No. 13/750,920 dated Apr. 8, 2015.
Response to Office Action in U.S. Appl. No. 13/750,920 dated Aug. 10, 2015.
Supplemental Response to Office Action in U.S. Appl. No. 13/750,920 dated Nov. 2, 2015.
Final Office Action in U.S. Appl. No. 13/750,920 dated Nov. 5, 2015.
Response to Office Action in U.S. Appl. No. 13/750,920 dated Feb. 11, 2016.
International Search Report and Written Opinion issued for International Application No. PCT/US2016/047165 dated Jan. 5, 2017, 13 pages.
Godwin, J., The Circulatory and Respiratory Systems, Z0250 Lab III, 2002, retrieved from: https://projects.ncsu.edu/cals/course/zo250/lab-3.html.

(56) References Cited

OTHER PUBLICATIONS

International Search Report and Written Opinion issued for PCT/US2018/012834 dated Mar. 15, 2018, 13 pages.
International Preliminary Report on Patentability issued in International Application No. PCT/US2016/024795 dated May 1, 2018, 10 pages.
International Preliminary Report on Patentability issued in International Application No. PCT/US2016/047165 dated May 1, 2018, 5 pages.
Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.
Blaney et al., Alteplase for the Treatment of Central Venous Catheter Occlusion in Children: Results of a Prospective, Open-Label, Single-Arm Study (The Cathflo Activase Pediatric Study).
Shah, T., Radiopaque Polymer Formulations for Medical Devices, MDDI Medical Diagnostic and Device Industry: Materials, 2001, retrieved from: https://www.mddionline.com/radiopaque-polymer-formulations-medical-devices.
International Preliminary Report on Patentability for PCT/US2016/047163 dated Dec. 25, 2018, 7 pages.
International Preliminary Report on Patentability for PCT/US2017/021188 dated Dec. 25, 2018, 9 pages.
International Search Report and Written Opinion for PCT/US2018/047372 dated Jan. 2, 2019, 8 pages.
International Search Report and Written Opinion for PCT/US2019/012727 dated Mar. 21, 2019, 12 pages.
International Search Report and Written Opinion for PCT/US2019/12745 dated Apr. 1, 2019, 10 pages.
EP 16777055.1 Extended Search Report dated Feb. 12, 2019, 7 pages.
EP 18725097.2 Extended Search Report dated Apr. 24, 2019, 9 pages.
EP 16860437.9 Extended Search Report dated May 17, 2019.
EP 16860409.8 Extended Search Report dated Jun. 27, 2019.

\* cited by examiner

SYSTEM FOR THE INTRAVASCULAR PLACEMENT OF A MEDICAL DEVICE

CROSS-REFERENCE TO RELATED APPLICATION

This application is the national phase of International Application No. PCT/US2013/071271, filed on Nov. 21, 2013, which claims priority to and the benefit of U.S. Provisional Application No. 61/728,862, filed on Nov. 21, 2012, the disclosures of which are incorporated herein by reference.

BACKGROUND

One known medical procedure is the catheterization process. During the catheterization process, a small incision is made in the skin at an entry site. A vascular tube called a sheath is inserted into the artery or vein and allows for easy catheter exchanges during the catheterization procedures. Guided by medical imaging, such as x-rays or other technology, the catheter is then inserted through the skin and maneuvered through the artery. Once the catheter is in place, contrast media may be injected into the blood vessel and an angiogram is taken of the blocked artery to help identify the site of the blockage. With medical imaging, such as x-rays or other technology, guidance, a thin wire called a guide wire may then be moved to the site to guide the placement of a diagnostic catheter, as well as any additional medical devices such as an angioplasty balloon catheter or a vascular stent, as desired.

There are angioplasty procedures that include the placement of a stent, a small, flexible tube made of plastic or wire mesh to support a damaged blood vessel wall. These stents may be self-expandable or balloon expandable, for example. Once the stent is in place, it may remain in the body permanently, acting as a scaffold for the damaged blood vessel. The guide wire, catheter, and any additional medical devices may then be removed from the patient through the entry site.

Technical difficulties in carotid artery stenting have arisen, particularly in the elderly population, due to arch vessel tortusity and aortic arch elongation and distortion. Stenting in this situation has resulted in adverse events, such as dislodgement of the delivery system from the target vessel during the procedure or failure to catheterize with large-caliber sheaths despite numerous attempts. In extreme cases, tears in the carotid artery and aortic arch can result. Also these excessive unsuccessful manipulations can cause plaque embolization from the aortic arch or carotid origin, and can result in a stroke during the procedure. One approach previously used has been obtaining through-and-through guidewire access using a surgical cutdown of the superficial temporal artery to facilitate the carotid artery stenting in these situations. The through-and-through access improves the ability to stabilize and manipulate the guidewire during the procedure and thus facilitates intervention, which may include carotid stenting, intracranial intervention, or other interventional procedures.

SUMMARY

A system for the intravascular placement of a medical device includes a guidewire having a first end and a second end, the first end having a microwhisk positional between a feeding state and a deployed state, a guidewire sheath surrounding the guidewire, and an anchoring device for cooperatively fixing the microwhisk relative to a patient.

The microwhisk may be various shapes. For example, the microwhisk may have a generally elliptical shape in its deployed state. In some embodiments, the microwhisk may have a bulbous shape having a rounded end that is joined to the guidewire by a tapering portion. Furthermore, the generally elliptical-shaped microwhisk may have a pointed end. In some embodiments, the microwhisk is disposed in the tip of a micro catheter and the pointed end of the microwhisk aids in steering the micro catheter through the vessel. The microwhisk may include at least two wire loops. In some embodiments, the microwhisk includes four wire loops, while in other embodiments the microwhisk has six wire loops. In embodiments, the continuity of the guidewire and the multiplicity of the wire loops allows the microwhisk to withstand the tension applied after it is anchored in place.

The anchoring device may include a handle portion and a pin portion. The pin portion may extend perpendicularly from the handle portion or any other suitable angle. The pin portion may, for example, be a needle. The needle may be between 21 gauge and 25 gauge inclusive. The handle portion of the anchoring device may be circular in shape and be divided into at least two hollow sections by at least one dividing member. In other embodiments, the handle portion may have two, three, four, or more dividing members configured to assist in aligning the pin portion under a fluoroscope or similar device. The handle portion may alternatively be a needle-hub.

Various aspects will become apparent to those skilled in the art from the following detailed description and the accompanying drawings.

BRIEF DESCRIPTION OF THE DRAWINGS

Reference is made to the accompanying drawings in which particular embodiments and further benefits of the invention are illustrated as described in more detail in the description below in which.

DETAILED DESCRIPTION

Figure 1:
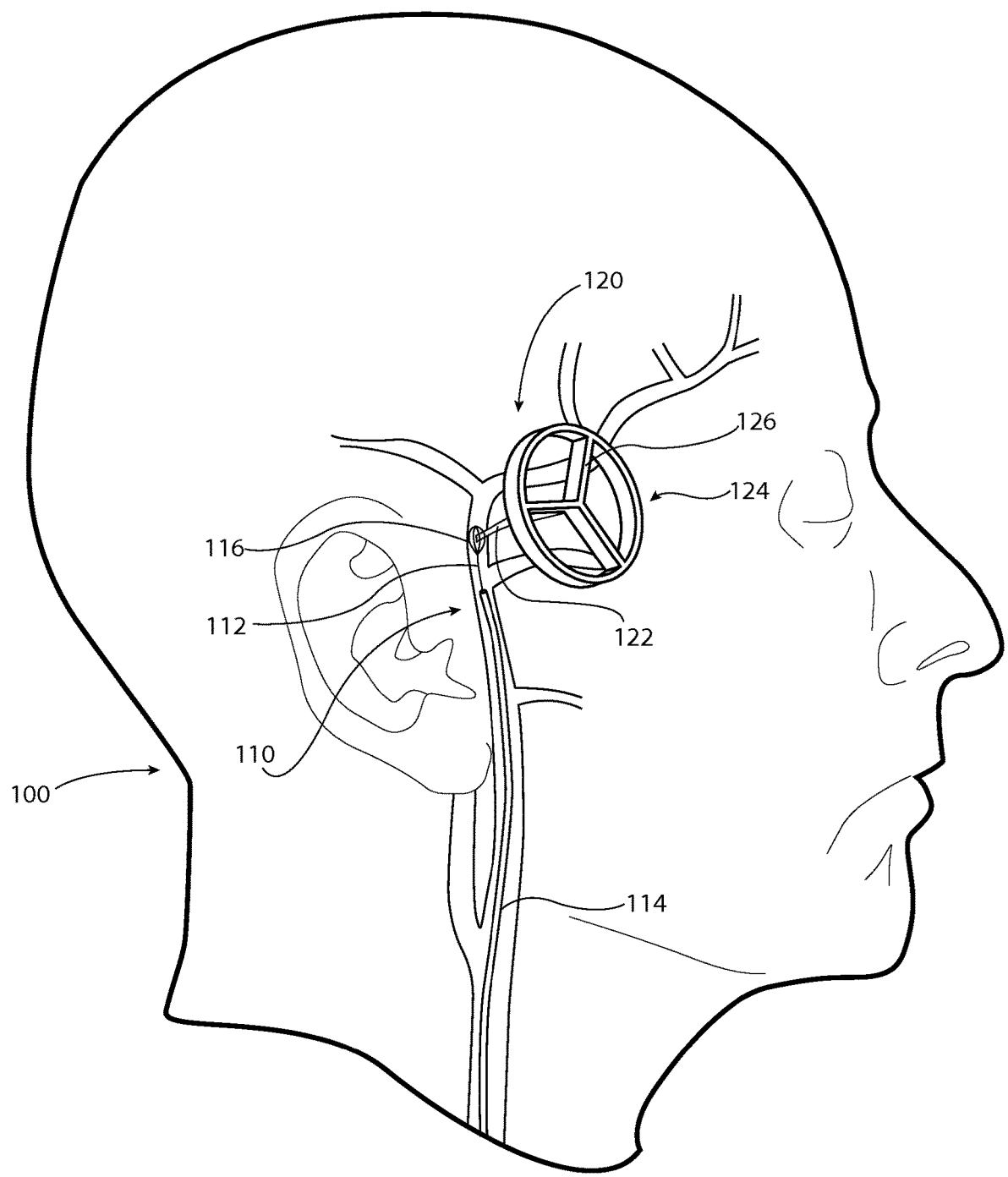
FIG. 1 is a side perspective view of a system for the intravascular placement of a medical device.

FIG. 1 shows a system for the intravascular placement of a medical device 100. The system 100 has a catheter apparatus component 110 including a guidewire 112 that is surrounded by a guidewire sheath 114. The guidewire sheath 114 is formed from a plastic, for example, a polymer or any other suitable, sterilizable material for a medical device. In some embodiments, the guidewire sheath 114 may be referred to as a micro catheter. The guidewire 112 has a microwhisk 116 on one end. The guidewire 112 may be composed of stainless steel which may be monofilament or braided. The guidewire 112 and the microwhisk 116 may instead be composed of a shape-memory alloy, such as nitinol. Alternatively, the shape-memory alloy may be a copper-aluminum-nickel, or a nickel-titanium, and may be created by alloying zinc, copper, gold and iron. Additionally to protect from contamination and promote flexibility, the guidewire 112 may be coated. A coated guidewire may be coated in Teflon, polyurethane, or another lubricious polymer.

Figure 5:
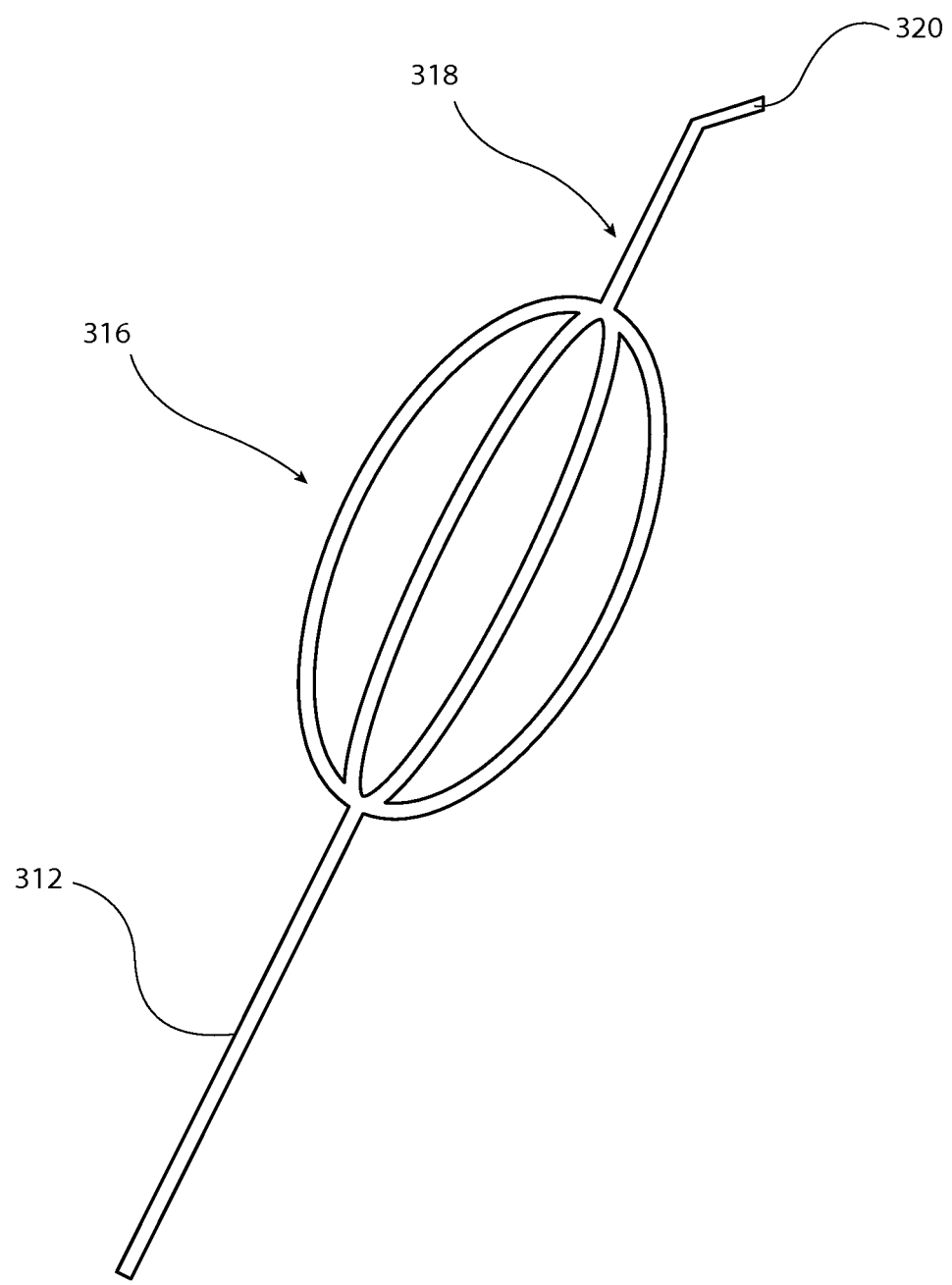
FIG. 5 is a perspective view of another embodiment of the system for the intravascular placement of a medical device.

During one exemplary catheterization process, a small incision is made in the skin at an entry site opening to a blood vessel, for example, the femoral artery. The catheter apparatus component 110, including the guidewire sheath 114 and its enclosed guidewire 112 and microwhisk 116, may then be guided into the blood vessel. The catheter apparatus component 110 must be flexible enough to travel through a tortuous path. For example, during the feeding process, a user observes the travel of the catheter apparatus component 110 by x-ray, or other technology as the catheter travels through the blood vessel. During the feeding process, the microwhisk 116 remains inside of the guidewire sheath 114. The catheter apparatus component 110 is fed and guided until it reaches the superficial temporal artery in the side of a patient's face, or other appropriate artery. The guidewire 112 may then be forced out of an end of the guidewire sheath 114, causing the microwhisk 116 to exit the guidewire sheath 114 and to deploy. As it is made from a shape memory alloy exhibiting a temperature response at approximately body temperature, the microwhisk 116 will then deploy to its original shape within the superficial temporal artery, or other appropriate artery. In an embodiment, such as illustrated in FIG. 5, a guidewire 312 has an end portion 318 extending from the microwhisk 316. The end portion of the guidewire may extend out of the catheter apparatus. In one embodiment, the end portion 318 is a flexible portion, and may be formed of the same material as the guidewire 312 on the opposite side of the microwhisk. In another embodiment, the end portion 318 includes an angled portion 320 that is angled relative to the axis of the guidewire to facilitate navigation of the guidewire and catheter through the vessel. In an embodiment, the angled portion is angled approximately 45 degrees relative to the axis of the guidewire.

In another exemplary process, the presently disclosed system may be used to access and navigate a type III aortic arch. A first catheter, such as a Simmons catheter or other catheter having a reverse curve or hook configuration, may be used to gain access to the ascending aorta and carotid artery and to secure the catheter in place. A micro catheter or guidewire sheath may then be advanced through the first catheter and advanced into the carotid artery. In one embodiment, a guidewire having a microwhisk is disposed within the micro catheter. The microwhisk has a tip that may be angled to facilitate selection of the external carotid artery and navigate the micro catheter to the desired location. Upon reaching the desired location, the microwhisk may be extended from the micro catheter allowing the microwhisk to expand and be secured in the vessel with an anchoring device as discussed below. In another embodiment, a conventional guidewire may be used to advance the micro catheter to the desired location. Upon reaching the desired location, the conventional guidewire may be removed, and the guidewire having a microwhisk may be inserted and advanced through the catheter until the microwhisk extends from the micro catheter and expands to be secured in the vessel. Once the microwhisk is secured, a carotid stenting or other procedure may be performed. In this manner the system may provide a stabilized platform for intervention in tortuous arteries of the head, neck or other extremities.

The system 100 also has an anchoring device 120 component. The device may include a pin portion 122 and a handle portion 124. Further, the handle portion may take on various forms, such as the embodiment shown in FIG. 1, wherein the handle portion 124 is circular and is divided into three hollow sections by dividing member 126. The dividing member may be positioned to facilitate use of the anchoring device under a fluoroscope such that the handle portion 124 assists in aligning the pin portion 122 at the desired location. In this manner, the handle portion 124 provides means for aligning the pin portion 122 with the desired target location to intersect with the microwhisk deployed in the vessel. In other embodiments, the handle portion 124 may be divided into four hollow sections.

Figure 2:
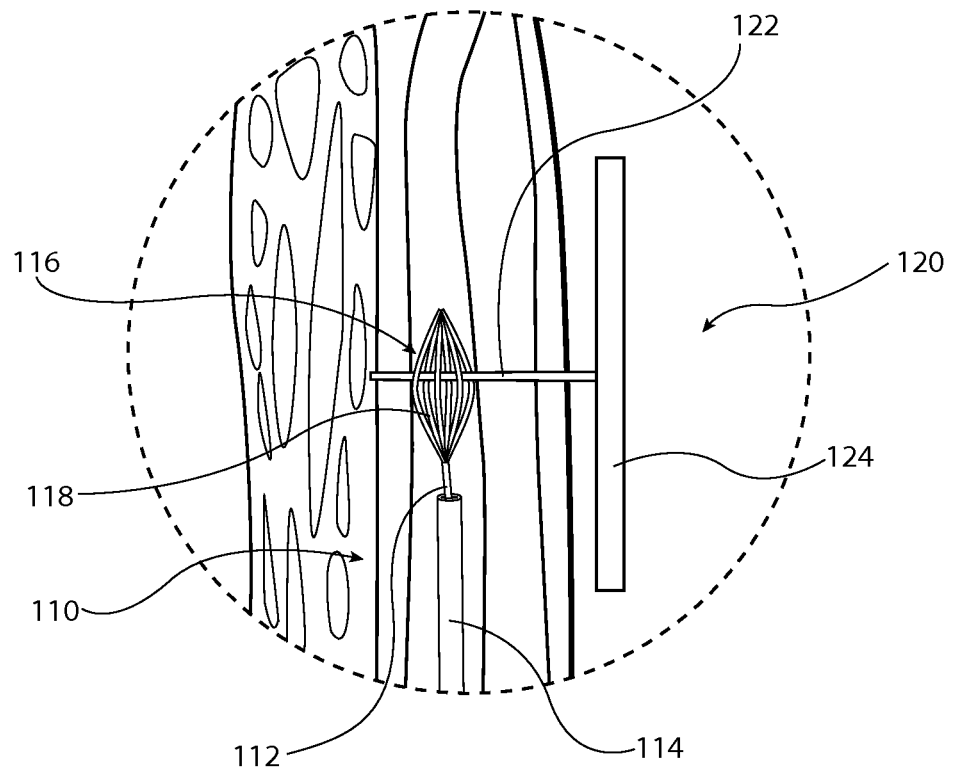
FIG. 2 is a partial cross-section view of the system for the intravascular placement of a medical device of in FIG. 1.

As shown in FIG. 2, the anchoring device 120 may include a pin portion 122 extending perpendicularly from the handle portion 124. The pin portion 122 may take the form of various instruments including, for example, a needle. The pin portion may be a needle less than or equal to 25 gauge. In addition, the pin portion may be a needle having a size between 21 gauge and 25 gauge. In another case, the pin portion may have a threaded portion, such as a screw tip. The threaded portion may assist in temporarily securing the pin portion, such as to a patients skull or other bone.

Figure 6:
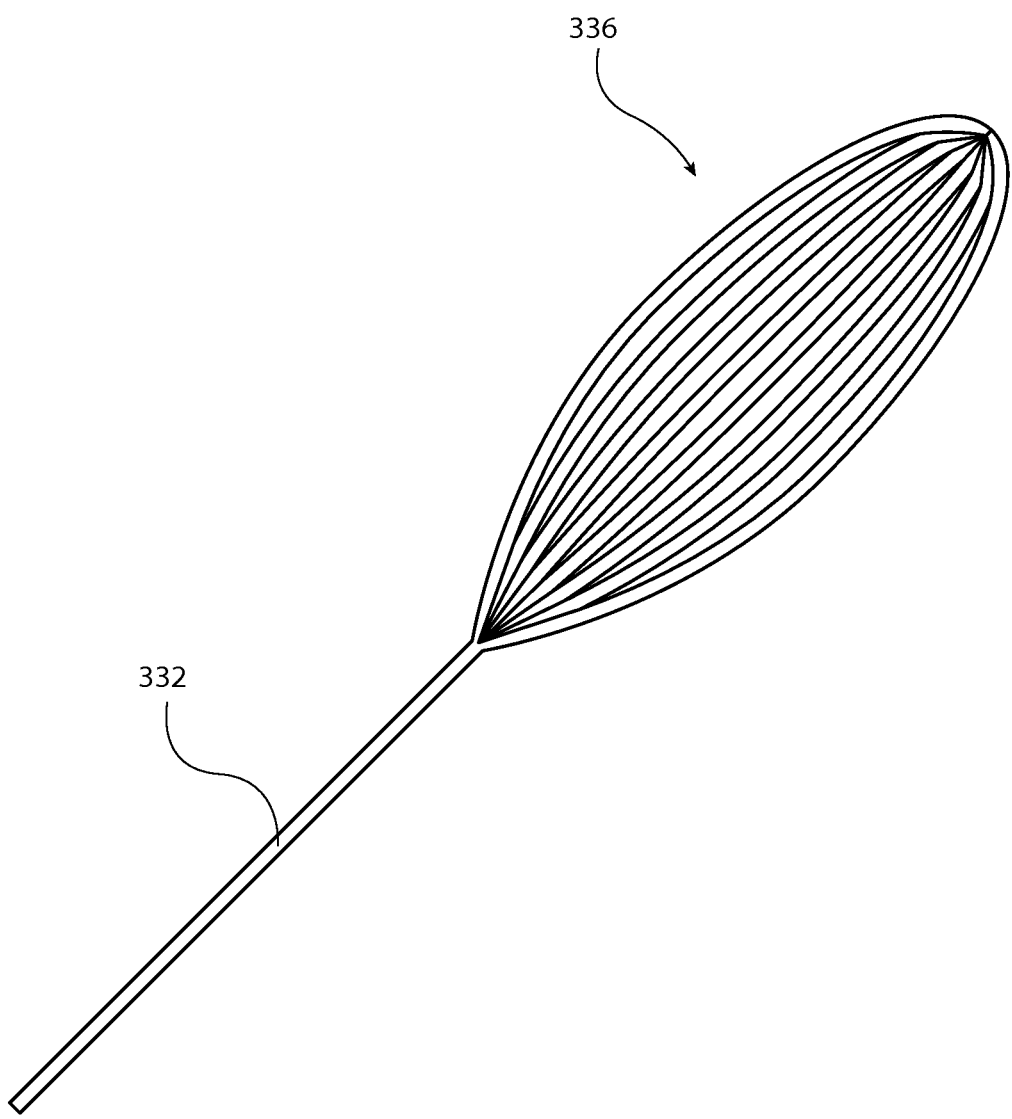
FIG. 6 is a side view of another embodiment of the system for the placement of a medical device

Referring again to FIG. 2, the microwhisk 116 may have at least two wire loops 118. In one embodiment, a first wire loop is oriented at a 90 degree angle to the second wire loop to form a cage configuration. In another example, the microwhisk may include three wire loops with each loop offset by approximately 60 degrees to form a cage configuration. In this manner, the microwhisk may be accessible regardless of rotation of the microwhisk within the artery or other vessel. In another embodiment, a guidewire 332 includes a microwhisk 336 having four wire loops such as illustrated in FIG. 6. In embodiments, each wire loop lies in a plane that passes through the axis of the guidewire. In this manner the wire loops form a microwhisk with a plurality of openings defined between successive wire loops. The openings may be parallel with the axis of the guidewire to facilitate capturing an anchoring device inserted substantially perpendicular to the axis of the guidewire.

The microwhisk 116 may have a generally elliptical shape in its deployed state. The size of the microwhisk may be selected for the artery or vessel. For example, for a superficial temporal artery, the microwhisk may have a diameter from 1.5 millimeters to 5 millimeters, however other sizes may also be used. When the microwhisk 116 is in its deployed state in the superficial temporal artery, the pin portion 122 of the anchoring device 120 is inserted through a skin surface on the patient's face by pushing, hammering, or screwing or any other insertion mechanism. In an example, the pin portion 122 is inserted substantially perpendicularly to the artery in which the microwhisk is positioned. Using medical imaging, such as x-rays or other technology, the pin portion 122 is guided to the location of the microwhisk 114, where the pin portion 122 passes through the wire loops 118 of the microwhisk 116, and an end of the pin portion 122 is inserted into the skull bone of the patient, thereby stabilizing the microwhisk 116 and guidewire 112. The stabilization of the catheter 110 increases the ease of the angioplasty and stenting processes.

Figure 3:
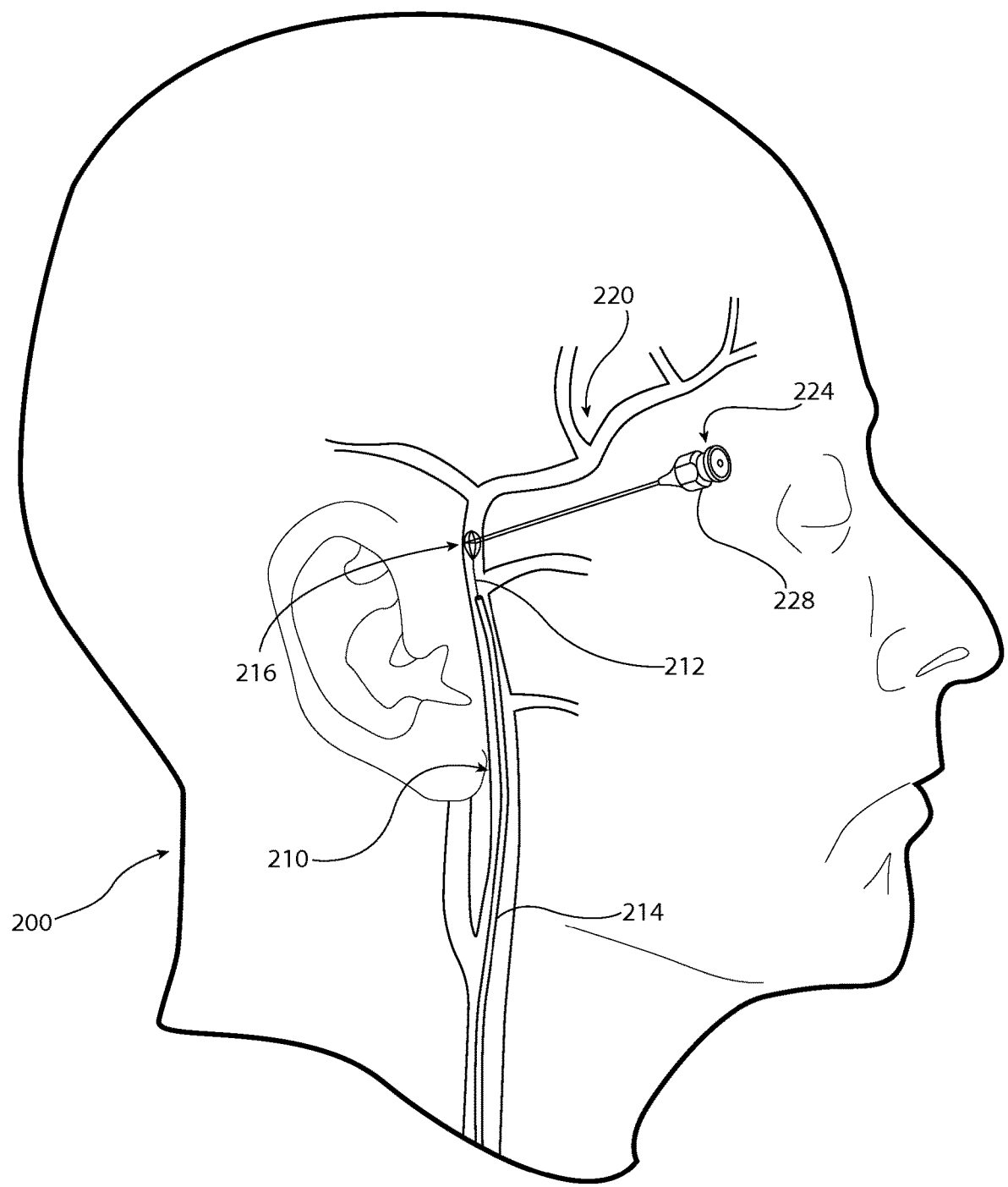
FIG. 3 is a side perspective view of another embodiment of the system for the intravascular placement of a medical device.

FIG. 3 shows an alternate embodiment of a system for the intravascular placement of a medical device 200. The system 200 has a catheter apparatus component 210 including a guidewire 212 that is surrounded by a guidewire sheath 214. The guidewire sheath 214 is formed from a plastic, for example a polymer or any other suitable, sterilizable material for a medical device. The guidewire 212 has a microwhisk 216 on one end. The guidewire 212 is composed of stainless steel which may be monofilament or braided. The guidewire 212 and the microwhisk 216 may instead be composed of a shape-memory alloy, such as nitinol. Alternatively, the shape-memory alloy may be a copper-aluminum-nickel, or a nickel-titanium, and may be created by alloying zinc, copper, gold and iron. Additionally, to protect from contamination and promote flexibility, the guidewire 212 may be coated. A coated guidewire may be coated in Teflon, polyurethane, or another lubricious polymer.

During one exemplary catheterization process, a small incision is made in the skin at an entry site opening to a blood vessel, for example, the femoral artery. The catheter apparatus component 210, including both the guidewire sheath 214 and its enclosed guidewire 212 and microwhisk 214, may then be guided into the blood vessel. The catheter apparatus component 210 must be flexible enough to travel through a tortuous path. For example, during the feeding process, a user observes the travel of the catheter apparatus component 210 by x-ray, or other technology as the catheter travels through the blood vessel. During the feeding process, the microwhisk 216 remains inside of the guidewire sheath 214. The catheter apparatus component 210 is fed until it reaches the superficial temporal artery in the side of a patient's face. The guidewire 212 may then be forced out of an end of the guidewire sheath 214, causing the microwhisk 216 to exit the guidewire sheath 214 and to deploy. As it is made from a shape memory alloy exhibiting a temperature response at approximately body temperature, the microwhisk 214 will then deploy to its original shape within the superficial temporal artery.

The system 200 also has an anchoring device 220 component. The device may include a pin portion 222 and a handle portion 224. Further, the handle portion may take on various forms, such as the embodiment shown in FIG. 3, wherein the handle portion 224 is a needle hub 228.

Figure 4:
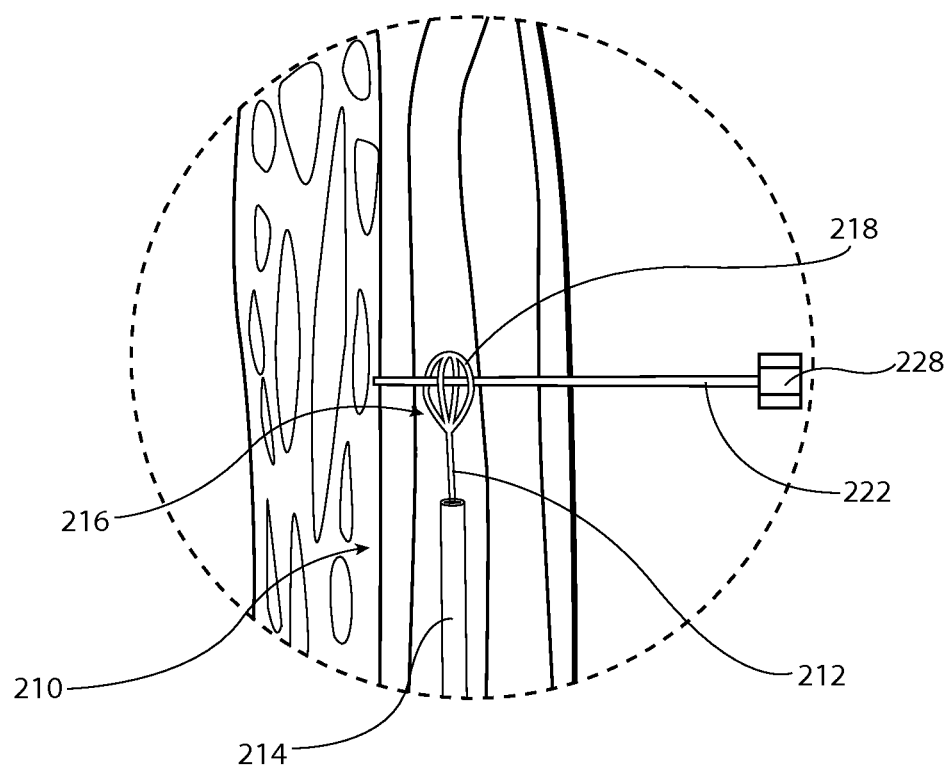
FIG. 4 is a partial cross-section view of the system for the intravascular placement of a medical device of FIG. 3.

As shown in FIG. 4, the anchoring device 220 may include a pin portion 222 extending perpendicularly from the handle portion 224. The pin portion 222 may take the form of various instruments including, for example, a needle. In one instance, the pin portion may be a needle less than or equal to 25 gauge. In another case, the pin may be a threaded fastener.

Referring again to FIG. 4, the microwhisk 216 may have at least two wire loops 218. The microwhisk 216 in its deployed state may have a generally elliptical shape with a pointed end. When the microwhisk 216 is in its deployed state in the superficial temporal artery, the pin portion 222 of the anchoring device 220 is inserted through a skin surface on the patient's face by pushing, hammering, or screwing or any other insertion mechanism. Using medical imaging, such as x-rays or other technology, the pin portion 222 is guided to the location of the microwhisk 214, where the pin portion 222 passes through the wire loops 118 of the microwhisk 116, and an end of the pin portion 222 is inserted into the skull bone of the patient, thereby stabilizing the microwhisk 216 and guidewire 212. The stabilization of the catheter 210 increases the ease of the angioplasty and stenting processes.

The systems and method described here may provide greater control over the manipulation and positioning of a guidewire for the placement of medical devices, such as stents. The improved control may improve the ability place medical devices, particularly in patients with arch vessel tortuosity and/or aortic arch elongation, both of which become progressively worse with age. Similarly, the presently disclosed system and method may improve access through tortuous iliac vessels. The present disclosure may assist in addressing the mechanical problems of prior methods wherein the vector forces produced while pushing the endovascular materials are out of line or even opposite to the vector forces necessary for appropriate delivery to the target vessel. Embodiments of this system may also be useful for lower extremity vascular interventions where there are acutely angled aortic bifurcations.

While certain embodiments have been described, it must be understood that various changes may be made and equivalents may be substituted without departing from the sprit or scope. In addition, many modifications may be made to adapt a particular situation or material to the teachings of the disclosure without departing from its spirit or scope.

What is claimed is:

1. A system for intravascular placement of a medical device for performing an angioplasty and stenting procedure, the system comprising:
    a guidewire comprising a first end and a second end opposite the first end, the first end of the guidewire comprising a microwhisk;
    a guidewire sheath surrounding the guidewire,
        wherein the guidewire sheath and guidewire comprising the microwhisk are configured to be inserted into a first artery via an arterial access and guided to a superficial peripheral artery,
        wherein the microwhisk is configured to transition between two states: a feeding state, where the microwhisk is within the guidewire sheath, and a deployed state, where the microwhisk is outside of the guidewire sheath, the microwhisk comprising a plurality of wire loops, and
        wherein, in the deployed state, each wire loop of the plurality of wire loops expands from the first end of the guidewire on exit from the guidewire sheath; and
    an anchoring device comprising only two portions: a handle portion and a pin portion fixed perpendicular to the handle portion, wherein the pin portion of the anchoring device comprises a threaded portion at a distal end opposite the handle portion to assist in anchoring the pin portion to a bone;
        wherein the pin portion is configured to penetrate through skin of a patient from outside a body of the patient at a location adjacent to the microwhisk, in the deployed state, wherein the pin portion is further configured to pass through a first side wall location of the superficial peripheral artery, and through at least one wire loop of the plurality of wire loops, in the deployed state;
        wherein the pin portion is further configured to pass through a second side wall location of the superficial peripheral artery, opposite the first side wall location, to provide stability to the microwhisk and the guidewire; and
        wherein the pin portion is further configured to be inserted into the bone of the patient outside of and adjacent to the superficial peripheral artery, thereby providing additional anchoring and stabilization to the microwhisk and the guidewire.

2. The system of claim 1, wherein the microwhisk comprises two wire loops.

3. The system of claim 1, wherein each of the plurality of wire loops comprises an elliptical shape, when the microwhisk is in the deployed state.

4. The system of claim 3, wherein the microwhisk comprises a pointed end.

5. The system of claim 4, wherein the pointed end includes an angled portion, wherein the angled portion is angled relative to an axis of the guidewire to facilitate navigation of the guidewire through a vessel.

6. The system of claim 1, wherein the pin portion comprises a needle.

7. The system of claim 6, wherein the needle is between 21 gauge and 25 gauge.

8. The system of claim 1,
wherein the pin portion is further configured to anchor the guidewire and a catheter used in the angioplasty and stenting procedure upon passing through the second side wall location of the superficial peripheral artery.

9. The system of claim 1, wherein the handle portion comprises a circular shape divided into at least two sections.

10. The system of claim 1, wherein the handle portion comprises a needle hub.

11. The system of claim 1, wherein the bone is a facial bone or a skull bone of the patient.

12. The system of claim 1, wherein the superficial peripheral artery comprises a superficial temporal artery.

13. The system of claim 1, wherein the first artery comprises a femoral artery.

14. An apparatus for intravascular placement of a medical device for performing an angioplasty and stenting procedure, the apparatus comprising:
a guidewire comprising a first end and a second end opposite the first end, the first end comprising a microwhisk;
a guidewire sheath surrounding the guidewire,
wherein the guidewire sheath and guide guidewire are configured to be inserted into a first artery via an arterial access and guided to a superficial peripheral artery,
wherein the microwhisk is configured to transition between two states: a feeding state, where the microwhisk is within the guidewire sheath, and a deployed state, where the microwhisk is outside of the guidewire sheath, the microwhisk comprising a plurality of wire loops, and wherein, in the deployed state, each wire loop of the plurality of wire loops expands on exit from the guidewire sheath during the deployed state; and an anchoring device comprising only two portions: a handle portion and a pin portion fixed perpendicular to the handle portion, wherein the pin portion of the anchoring device comprises a threaded portion at a distal end opposite the handle portion to assist in anchoring the pin portion to a bone,
wherein the pin portion is configured to penetrate through skin of a patient from outside a body of the patient at a location adjacent to the microwhisk, in the deployed state, through a first side wall location of the superficial peripheral artery, and through at least one wire loop of the plurality of wire loops of the microwhisk in the deployed state,
wherein the pin portion is further configured to pass through a second side wall location of the superficial peripheral artery, opposite the first side wall location, to provide stability to the microwhisk and the guidewire, and
wherein the pin portion is further configured to be inserted into the bone of the patient adjacent to the superficial artery, thereby anchoring and stabilizing the microwhisk, the guidewire and a catheter used in the angioplasty and stenting procedure.

15. The apparatus of claim 14, wherein the guidewire and the microwhisk are formed from a shape-memory alloy.

16. The apparatus of claim 15, wherein the shape-memory alloy comprises nitinol.

17. The apparatus of claim 14, wherein each wire loop of the plurality of wire loops comprises an elliptical shape when the microwhisk is in the deployed state.

18. The apparatus of claim 14,
wherein the pin portion provides stabilization to the guidewire because the pin portion is inserted through the at least one wire loop of plurality of wire loops of the microwhisk and the first wall and the second wall of the superficial artery.

19. The system of claim 14, wherein the superficial peripheral artery of the patient is a superficial temporal artery.

20. The apparatus of claim 14, wherein the bone is a facial bone or a skull bone of the patient.

21. The apparatus of claim 14, wherein the first artery comprises a femoral artery.

22. The apparatus of claim 14, wherein the first artery comprises a radial artery.

* * * * *